(12) United States Patent
Vartuli et al.

(10) Patent No.: US 7,173,158 B2
(45) Date of Patent: *Feb. 6, 2007

(54) MIXED METAL OXIDE CONTAINING SULFUR

(75) Inventors: James Clarke Vartuli, Schwenksville, PA (US); Doron Levin, Annandale, NJ (US); Stephen John McCarthy, Center Valley, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/141,483

(22) Filed: May 31, 2005

(65) Prior Publication Data

US 2006/0269462 A1   Nov. 30, 2006

(51) Int. Cl.
*C07C 29/00* (2006.01)
*C07C 29/10* (2006.01)
*C07C 31/10* (2006.01)

(52) U.S. Cl. .................. 568/700; 568/889; 568/907; 585/638; 585/639

(58) Field of Classification Search ........... 423/511, 423/512.1, 518; 568/700, 889, 907; 585/638, 585/639
See application file for complete search history.

(56) References Cited

U.S. PATENT DOCUMENTS

| | | | |
|---|---|---|---|
| 4,521,638 A | 6/1985 | Kida et al. ............ 585/640 |
| 4,691,073 A | 9/1987 | Michaelson ........... 585/639 |
| 5,171,920 A | 12/1992 | Chaumette et al. ..... 585/640 |
| 5,177,301 A | 1/1993 | Knifton ................. 585/855 |
| 5,254,785 A | 10/1993 | Rosenfeld et al. ..... 585/640 |
| 5,403,964 A * | 4/1995 | Saleh et al. ........... 568/907 |
| 5,478,543 A | 12/1995 | Murota et al. ......... 423/263 |
| 5,518,658 A * | 5/1996 | Rossner et al. ....... 252/301.4 S |
| 5,518,699 A | 5/1996 | Kashnitz et al. ....... 422/211 |
| 5,532,198 A | 7/1996 | Chopin et al. ......... 502/304 |
| 5,580,536 A | 12/1996 | Yao et al. .............. 423/263 |
| 5,582,785 A | 12/1996 | Yao et al. .............. 264/60 |
| 5,607,892 A | 3/1997 | Chopin et al. ......... 502/304 |
| 5,609,793 A * | 3/1997 | Yokota et al. ........ 252/301.4 S |
| 5,712,218 A | 1/1998 | Chopin et al. ......... 502/304 |
| 5,747,401 A | 5/1998 | Cuif ..................... 501/103 |
| 5,908,800 A | 6/1999 | Bonneau et al. ....... 501/103 |
| 6,133,194 A | 10/2000 | Cuif et al. ............. 502/506 |
| 6,150,299 A | 11/2000 | Umemoto et al. ...... 502/304 |

(Continued)

FOREIGN PATENT DOCUMENTS

JP         6072904         3/1994

(Continued)

OTHER PUBLICATIONS

P.B. Meunier and P. Chaumette, *High-purity isobutene production by decomposition of MTBE*, Revue de l'Institut Français du Pétrole, 1991, vol. 46.

(Continued)

*Primary Examiner*—Timothy C. Vanoy
(74) *Attorney, Agent, or Firm*—Andrew B. Griffis

(57) ABSTRACT

The invention relates to a composition of matter comprising at least one metal from Group 3, at least one metal from Group 4, sulfur and oxygen, particularly useful as a catalyst for ether decomposition to alkanols and alkenes.

11 Claims, 4 Drawing Sheets

Plot of Peformance (maximum IPA yield) vs. amount of sulfur in catalyst.

U.S. PATENT DOCUMENTS

| | | | |
|---|---|---|---|
| 6,255,242 B1 | 7/2001 | Umemeoto et al. | 501/103 |
| 6,291,719 B1 | 9/2001 | Gao et al. | 568/596 |
| 6,297,406 B1 | 10/2001 | Levin et al. | 568/798 |
| 6,319,876 B1 | 11/2001 | Maier | 502/178 |
| 6,506,705 B2 | 1/2003 | Blanchard et al. | 502/300 |
| 6,552,236 B2* | 4/2003 | Sakuth et al. | 568/907 |
| 6,906,229 B1* | 6/2005 | Burton | 568/907 |
| 2005/0177009 A1* | 8/2005 | Levin et al. | 568/907 |

FOREIGN PATENT DOCUMENTS

| WO | WO 2005/066101 | 7/2005 |
|---|---|---|

OTHER PUBLICATIONS

Morterr et al., *Catalytic Activity and Some Related Spectral Features of Ytrria-Stabilised Cubic Sulfated Zirconia*, Catalysts Letters, vol. 73, No. 2-4, pp. 113-119, (2001).

Signoretto, Michala, *One the Role of the Calcination Step in the Preparation of Active (Superacid) Sulfated Zirconia Catalysts*, Catalysis Letters, vol. 41, pp. 101-109, (1996).

Morterrra et al., *Acetonitrile Adsorption as an IR Spectroscopic probe for Surface Acidity/Basicity of Pure and Modified Zironcias*, Phys. Chem.. Chem. Phys., vol. 4, pp. 676-687, (2002).

* cited by examiner

Figure 1. Plot of Peformance (maximum IPA yield) vs. amount of sulfur in catalyst.

MIXED METAL OXIDE CONTAINING SULFUR

FIELD OF THE INVENTION

The invention relates to a composition of matter comprising at least one metal from Group 3, at least one metal from Group 4, sulfur and oxygen, particularly useful as a catalyst for ether decomposition to alkanols and alkenes.

BACKGROUND OF THE INVENTION

Mixed oxides of Group 3 (including the Lanthanides and Actinides) and Group 4 metals are known to be useful in catalyzing oxidation-reduction reactions such as exhaust gas purification.

The use of such catalysts in the purification of exhaust gases, particularly gases produced by an internal combustion engine, have been described, for instance, in U.S. Pat. Nos. 5,478,543; 5,518,699; 5,532,198; 5,580,536; 5,582,785; 5,607,892; 5,712,218; 5,747,401; 5,908,800; 6,133,194; 6,150,299; 6,255,242; 6,291,719; 6,319,876; 6,506,705, and 6,605,565

Various catalyst have been proposed for the decomposition of ethers, have been described, for instance, in U.S. Pat. Nos. 4,691,073; 4,254,290; 4,320,232; 4,521,638; 4,398,051; 4,357,147. "Production D'Isobutene de Haute Pureté par Décomposition du MTBE" by P. B. Meunier et al. in Revue de L'Institut Francais du Petrole, vol. 46, No. 3, May 19991, pages 361 to 387, U.S. Pat. Nos. 5,254,785, 5,177, 301, 5,171,920 and Japanese Published Patent Application No. JP-A-06072904.

Unpublished International Application No. PCT/US2004/041546 discloses a process for selectively converting a dialkyl ether to the corresponding alkene and alkanol, the process comprising contacting a feed containing at least one dialkyl ether with a catalyst comprising an acidic mixed metal oxide having the following composition:

$$X_m Y_n Z_p O_q$$

where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p and q are the atomic ratios of their respective components and, when m is 1, n is from 0.01 to 0.75, p is from 0 to 0.1, and q is the number of oxygen atoms necessary to satisfy the valence of the other components. The mixed oxides preferably contain sulfur, typically present in an amount of up to 5 wt %, such as up to 1 wt %, of the final mixed oxide composition. The mixed oxides can prepared by impregnation or by co-precipitation from a liquid mixture containing a source of Group 4 metal ions and a source of Group 3 and/or Group 6 metal ions.

One of the key challenges in developing this technology is the development of a catalyst that selectively converts the ether to the alcohol without subsequently dehydrating the alcohol to the corresponding olefin. The catalytic performance of the ceria-zirconia catalyst is influenced by the method of making of the ceria-zirconia mixed metal oxide, and factors such as the ceria content, pH of precipitation, gel aging, and calcination temperature all affect the catalyst performance. The present inventors, however, have discovered a cerium-sulfur-zirconium catalyst that has the desired level of activity and selectivity for this reaction.

SUMMARY OF THE INVENTION

The invention is directed to a mixed metal oxide catalyst compositions having the following empirical formula (1):

$$X_m Y_n S_p O_q \tag{1}$$

where X is at least one metal selected from Group 4 of the Periodic Table of Elements, preferably zirconium, Y is at least one metal selected from Group 3 (including the Lanthanides and Actinides) of the Periodic Table of Elements, preferably cerium, S is sulfur, and O is oxygen; m, n, p and q are the atomic ratios of their respective components and, when m is 1, n is from about 0.01 to about 0.75, preferably from about 0.01 to about 0.35; p is from about 0.01 to about 0.50, preferably from about 0.05 to about 0.35, more preferably from about 0.10 to about 0.30, still more preferably from about 0.10 to about 0.20; and q is the number of oxygen atoms necessary to satisfy the valence of the other components.

X and Y are preferably zirconium and cerium, respectively.

It is also preferred that sulfur be present in the compound according to formula (1) in the amount of from 0.50 to 1.25 wt %, more preferably in the amount of from 0.65 to less than 1.00 wt %, and still more preferably in the amount of from 0.65 to 0.85 wt %.

In a preferred embodiment, the invention is directed to a composition comprising the compound of formula (1) above having the proper distribution of Bronsted and Lewis acid sites.

In another preferred embodiment, the invention is characterized by the presence of surface sulfur species having S=O stretching vibration in the region of 1420–1300 cm$^{-1}$, preferably 1390–1365 cm$^{-1}$.

In still another preferred embodiment, the invention is characterized by having a shift in $\upsilon$(CN) of adsorbed deuterated acetonitrile to greater than 2260 cm$^{-1}$.

In yet another preferred embodiment, the invention is directed to a process for the decomposition of ethers to the corresponding alkanols and alkenes and still more preferably to a process for the production of IPA from IPE, and also still more preferably to a process for the production of sec-butyl alcohol from sec-butyl ether.

It is an object of the invention to provide one or more compositions for each of the above-recited embodiments.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

Figure 1:
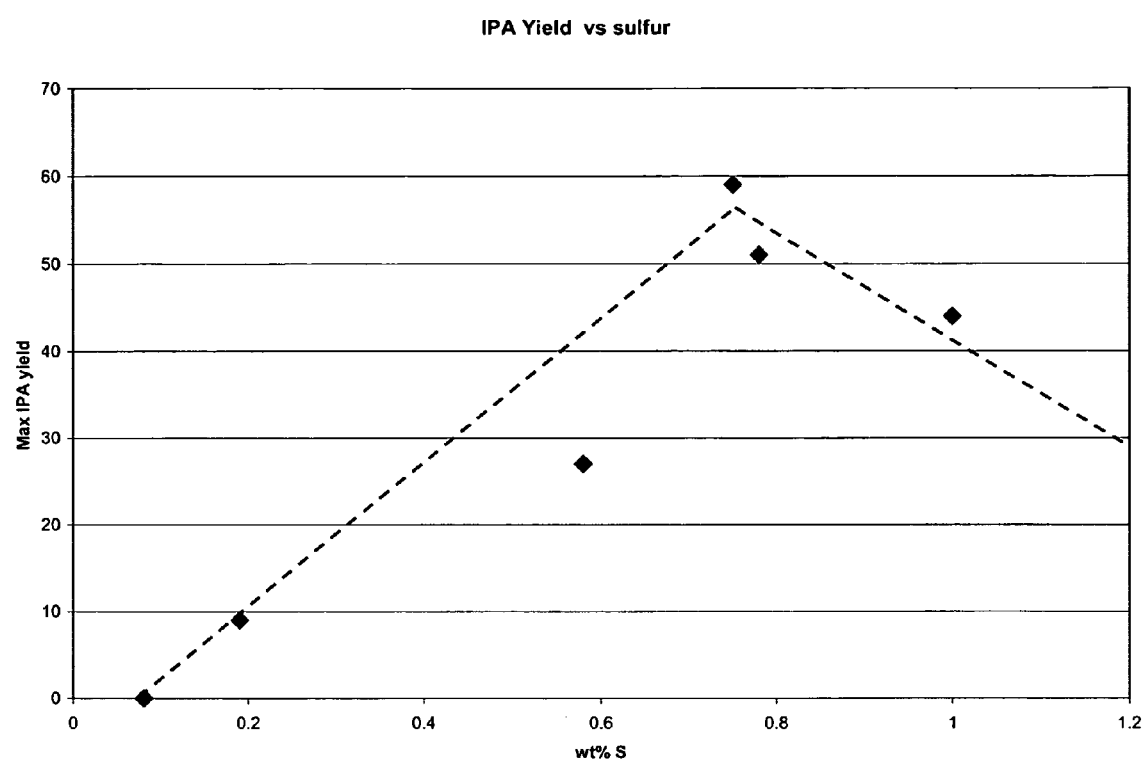
FIG. 1 is a plot of IPA yield from the decomposition of IPE versus the percent sulfur in a catalyst according to formula (1).

According to the invention, the mixed metal oxide catalyst composition of the invention has the following empirical formula (1):

$$X_m Y_n S_p O_q \quad (1)$$

where X is at least one metal selected from Group 4 of the Periodic Table of Elements, Y is at least one metal selected from Group 3 (including the Lanthanides and Actinides) of the Periodic Table of Elements, and S is sulfur; m, n, p and q are the atomic ratios of their respective components and, when m is 1, n is from about 0.01 to about 0.75, preferably from about 0.01 to about 0.35; p is from about 0.01 to about 0.50, preferably from about 0.05 to about 0.35, more preferably from about 0.10 to about 0.30, still more preferably from about 0.10 to about 0.20; and q is the number of oxygen atoms necessary to satisfy the valence of the other components. The Periodic Table of Elements referred to herein is the Periodic Table using the "new" notation described in Chemical and Engineering News 63(5), 27, 1985, which numbers the groups from 1 to 18.

Suitable Group 3 metals include scandium, yttrium and lanthanum, and metals from the Lanthanide or Actinide series, such as cerium, praseodymium, neodymium, samarium, europium, gadolinium, terbium, dysprosium, holmium, erbium, thulium, ytterbium, lutetium and thorium. The most preferred Group 3 metal is cerium.

Suitable Group 4 metals include titanium, zirconium and hafnium, with zirconium being most preferred.

In a preferred embodiment, X is zirconium and Y is cerium.

While a primary factor for the acidity and selectivity of this mixed metal oxide catalyst appears to be linked with the concentration of all three components in the preparation, the presence of sulfur is critical. In a preferred embodiment, in addition to the above characterization, sulfur should be present in the compound according to formula (1) in the amount of from 0.50 to 1.25 wt %, more preferably in the amount of from 0.65 to less than 1.00 wt %, and still more preferably in the amount of from 0.65 to 0.85 wt %.

In the preferred process for making the compound according to formula (1), the Group 3 and 4 metals are coprecipiated from solution in the presence of sulfur, preferably as sulfate. In a more preferred embodiment, the sulfur content is obtained by using either a sulfate salt of cerium or by addition of other sulfur containing salts, for example ammonium sulfate.

X and Y are provided by separate salts, each preferably highly soluble in the solution, which is preferably an aqueous solution. The slurry comprising the coprecipitate is optionally aged by, for instance, storage in a steambox or autoclave for a predetermined period of time and temperature, such as about 50 to about 250° C., preferably about 75 to about 150° C., and from about 5 to about 100 hours, preferably from about 24 hours to about 72 hours. The coprecipitate may be conveniently recovered by filtration, followed by drying and then calcination of the resulting catalyst precursor in the manner described below.

The liquid mixture can be prepared by combining a first liquid solution comprising a source of Group 4 metal ions with a second liquid solution comprising a source of Group 3 metal ions, wherein the combination takes place under conditions sufficient to cause co-precipitation of the catalyst precursor as a solid from the liquid medium. It is preferred that the two solutions be combined by nozzle mixing as is per se known in the art. Alternatively, the source of the Group 4 metal ions and the source of the Group 3 metal ions may be combined into a single solution. This solution may then be subjected to conditions sufficient to cause co-precipitation of the catalyst, such as by the addition of a precipitating reagent, such as ammonium hydroxide and the like, to the solution. In a preferred embodiment, an aqueous solution of a base is added so that the pH of the solution containing X, Y, and S is caused to be about greater than 7 to at or below 9, preferably about 8.

Suitable sources of the metal ions for the coprecipitation include compounds such as oxychlorides, chlorides, alkoxides, sulfates and nitrates. Preferably, at least one of the metals is present as a sulfate and/or a source of sulfate ions is added to the liquid mixture from which the catalyst precursor is precipitated.

Where the Group 4 metal includes zirconium, the preferred source of zirconium is zirconyl nitrate.

Where the Group 3 metal includes cerium, the preferred source of cerium is a cerium sulfate-sulfuric acid complex or more preferably cerium nitrate.

Calcination of the catalyst precursor is effected, typically in an oxidizing atmosphere, at a temperature of at least 400° C., such as at least 500° C., for example from about 500° C. to about 800° C. The calcination time may be up to 48 hours, such as for about 0.5 to about 24 hours, for example for about 1 to about 10 hours. Where the catalyst precursor contains sulfate ions, the calcination conditions should be controlled so as to retain the desired sulfur level in the final catalyst composition The empirical formula given above and ranges for atomic ratios are for the compounds according to the invention after calcination.

The mixed oxide compositions of the invention are useful as catalysts in a variety of chemical reactions.

It should be understood that the present invention is directed to a composition of matter which comprises the active phase of a catalyst or catalyst system and that various other materials, for example cocatalysts, binders, supports, matrices, and the like, may be combined for purposes such as to provide strength, porosity, and the like, to make the final material actually used, and that one of ordinary skill in the art in possession of the present disclosure could readily make such final material without more than routine experimentation.

The mixed oxides of the present invention are useful catalysts in a variety of chemical reactions, in particular in the decomposition of ethers into the corresponding alcohols and/or olefins. Accordingly, the present invention also relates to a process for decomposing ethers to their corresponding alcohols and ethers, using a mixed oxide as described above as catalyst.

The ether decomposition process of the invention involves contacting an ether-containing feed with a mixed metal oxide catalyst described above under conditions effective to convert the ether to an olefin and an alcohol. Suitable ethers for use in the process of the invention include those having the formula

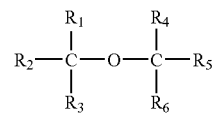

wherein $R_1$, $R_2$, $R_3$, $R_4$, $R_5$ and $R_6$ are the same or different and are selected from hydrogen, alkyl, arylalkyl and alkylaryl species, each preferably having up to 20 carbon atoms, with the proviso that, when all the substituents $R_1$ through $R_6$ are hydrogen, i.e. the compound is dimethyl ether, the product is principally methanol.

In general, the conditions employed are not narrowly defined and depend not only on the ether starting material but also on the desired conversion rate and product selectivity. Typically, however, the conditions will include a temperature of about 50° C. to about 320° C., a pressure of about 0 kPa (pressures used herein are gauge pressures unless otherwise specified) to about 3500 kPa, and a weight hourly space velocity (WHSV) of about 0.1 hr$^{-1}$ to about 25 hr$^{-1}$; such as a temperature of about 100° C. to about 275° C., a pressure of about 0 kPa to about 2400 kPa and a weight hourly space velocity (WHSV) of about 0.5 hr$^{-1}$ to about 10 hr$^{-1}$.

In one practical embodiment, the ether-containing feed contains methyl tert-butyl ether (MTBE) and is produced by reacting a mixed butene stream with methanol. After separation, the present process is used to selectively decompose the resultant MTBE to iso-butene and methanol. A similar process can be used with mixed pentenes to produce tert-amyl methyl ether (TAME) for selective conversion to isoamylene and methanol. In this embodiment, suitable ether decomposition conditions include a temperature of about 100° C. to about 200° C. and a pressure of about 0 kPa to about 1000 kPa and a weight hourly space velocity (WHSV) of about 1 hr$^{-1}$ to about 10 hr$^{-1}$.

In yet another practical embodiment, the ether-containing feed contains sec-butyl ether (SBE) and is produced as a by-product of the hydration of butene to produce sec-butanol. One possible method of disposal of the SBE is as a fuel, for example by addition to motor vehicle gasoline, but, not only may this be subject to environmental regulation, it also leads to a loss of butenes as a lower-valued component. Moreover, the SBE may not be readily isolatable as a single component stream by conventional separation techniques, and may form a mixture with close-boiling butene oligomers composed mostly of $C_8$ olefins formed by dimerization of the butenes. However, while the $C_8$ olefins, being highly branched, would make a good high-octane additive to gasoline, environmental regulation may require elimination of the SBE from this stream. Accordingly, a preferred decomposition pathway for SBE is by conversion to sec-butanol and 2-butene in a process that limits oligomerization of the butene formed and of the $C_8$ olefins present.

The catalyst compositions of the present invention are active for the selective conversion of SBE to sec-butanol and 2-butene with limited oligomerization of the resultant butenes and limited oligomerization/isomerization of any $C_8$ olefins present. At higher temperatures, some or all of the sec-butanol may be dehydrated to 2-butene according to a reaction of the type indicated above as reaction (2). In this embodiment, preferred ether decomposition conditions include a temperature of about 150° C. to about 275° C., a pressure of about 0 kPa to about 700 kPa, and a weight hourly space velocity (WHSV) of about 0.5 hr$^{-1}$ to about 10 hr$^-$. Conveniently, the feed to the catalyst includes water in addition to the SBE, with the molar ratio of water to SBE typically ranging from 0 to 3, such as about 0.5 to about 2, for example about 1.5.

In another embodiment, the catalyst made by the process of the invention may be used for the purification of exhaust gases produced by an internal combustion engine, e.g., for use in catalytic converters, by contacting such a gas with the catalyst according to the present invention.

In a preferred embodiment, the ether-containing feed contains isopropyl ether (IPE). In a more preferred embodiment the IPE is produced as a by-product of propylene hydration, in a process for the manufacture of isopropyl alcohol (IPA). Some IPA processes involve contacting propylene with sulfuric acid. This can be accomplished with gas/liquid absorption or liquid/liquid extraction. While these processes have been utilized for several decades, some improvements have been made. The improvements include a process configuration that utilizes a unique combination of plug flow, bubble column, and closed stirred tank reactor reaction sections to achieve high conversion of dilute or concentrated propylene. Also spargers custom designed for the propylene/sulfuric acid absorption/extraction section can be used. Further, loop reactors may be preferred to improve mixing integrity.

One possible method of disposal of IPE produced as a side-product of IPA is as a fuel but, not only may this be subject to environmental regulation, but also a higher economic value can be achieved by selective decomposition of the IPE to propylene and IPA. The optimal pathway for this reaction is therefore shown by reaction (1):

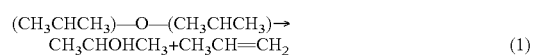

$$(CH_3CHCH_3)—O—(CH_3CHCH_3) \rightarrow CH_3CHOHCH_3 + CH_3CH=CH_2 \quad (1)$$

The challenge faced in the catalytic decomposition of IPE is two-fold, firstly, minimizing the dehydration of IPA formed by reaction (1) to propylene according the reaction (2):

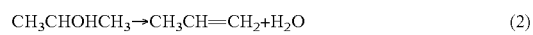

$$CH_3CHOHCH_3 \rightarrow CH_3CH=CH_2 + H_2O \quad (2)$$

and secondly, minimizing oligomerization of the propylene formed according to reaction (3):

$$xCH_3CH=CH_2 \rightarrow (C_3H_6)_x \quad (3).$$

Although each of reactions (1)–(3) is acid catalyzed, the process of the invention is effective to decompose IPE according to reaction (1) while reducing IPA dehydration and propylene oligomerization. Preferably, the conditions used to effect IPE decomposition include a temperature of about 100° C. to about 320° C., such as about 200° C. to about 300° C., for example about 240° C. to about 280° C.; a pressure of about 100 kPa to about 3550 kPa, such as about 400 kPa to about 1800 kPa, for example about 700 kPa to about 1500 kPa, a weight hourly space velocity (WHSV) of about 0.5 hr$^{-1}$ to about 10 hr$^{-1}$, such as about 3 hr$^{-1}$ to about 10 hr$^{-1}$, for example about 7 hr$^{-1}$. Conveniently, the feed to the catalyst includes water in addition to the IPE, with the molar ratio of water to IPE typically ranging from 0 to 3, such as about 0.5 to about 2, for example about 1.5.

The processes of the invention may be conducted in a stationary or fluidized bed, and may take place continuously or batch-wise.

The processes of the invention may be conducted using pure ether feedstocks, or they may include a diluent such as nitrogen, argon, carbon dioxide, alkanes, and the like. In a preferred embodiment, water may be added together with the ether feed to minimize dehydration of the resultant alcohols.

Several examples of the preparation of compounds according to the present example are given below.

Experimental

The following examples are meant to illustrate the present invention and provide a comparison with other methods. Numerous modifications and variations are possible and it is to be understood that within the scope of the appended claims, the invention may be practiced otherwise than as specifically described herein.

Examples 1 through 6 describe the synthesis of the ceria/zirconia catalysts.

EXAMPLE 1

Five hundred grams of zirconyl chloride hydrate, $ZrOCl_2 \cdot xH_2O$, and 14 grams of cerium (IV) sulfate, $Ce(SO_4)_2$ were dissolved with stirring in 3.0 liters of distilled water. A second solution containing 260 grams of concentrated $NH_4OH$ and 3.0 liters of distill water was prepared. These two solutions were combined at the rate of 50 ml/min using a nozzle mixing. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and stored as a filtercake. The filtercake is dried overnight at 250° F. Thereafter the filtercake is calcined at 700° C. for a total of 3 hours in flowing air and then allowed to cool. The elemental analyses are shown in Table 1.

EXAMPLE 2

Five hundred grams of zirconyl chloride hydrate, $ZrOCl_2 \cdot xH_2O$, and 140 grams of cerium (IV) sulfate, $Ce(SO_4)_2$ were dissolved with stirring in 3.0 liters of distilled water. A second solution containing 260 grams of concentrated $NH_4OH$ and 3.0 liters of distill water was prepared. These two solutions were combined at the rate of 50 ml/min using a nozzle mixing. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and stored as a filtercake. The filtercake is dried overnight at 250° F. Thereafter the filtercake is calcined at 700° C. for a total of 3 hours in flowing air and then allowed to cool. The elemental analyses are shown in Table 1.

EXAMPLE 3

One hundred and twenty-five grams of zirconyl chloride hydrate, $ZrOCl_2 \cdot xH_2O$, and 4.6 grams of cerium (III) nitrate hexahydrate, $Ce(NO_3)_3 6H_2O$ were dissolved with stirring in 0.5 liters of distilled water. A second solution containing 50 grams of concentrated $NH_4OH$, 54 grams of ammonium sulfate, $(NH_4)_2SO_4$, and 0.5 liters of distill water was prepared. These two solutions were combined at the rate of 50 ml/min using a nozzle mixing. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and stored as a filtercake. The filtercake is dried overnight at 250° F. Thereafter the filtercake is calcined at 700° C. for a total of 3 hours in flowing air and then allowed to cool. The elemental analyses are shown in Table 1.

EXAMPLE 4

One hundred and thirty one grams of $ZrO(NO_3)_2 \cdot xH_2O$ and 72.9 grams of $Ce(NO_3)_4$ were dissolved with stirring in 483 grams of distilled water. A second solution containing 109.8 grams of concentrated $NH_4OH$ and 528 grams of distilled water was prepared. These two solutions were combined at the rate of 50 ml/min using a nozzle mixing. The pH of the final composite was adjusted to approximately 8 by the addition of concentrated ammonium hydroxide. This slurry, having a solids content of about 7%, and was then aged in an autoclave at 100° C. for 72 hours. The product formed was recovered by filtration, washed with excess water, and stored as a filtercake. The filtercake was dried overnight at 120° C. Thereafter, the filtercake was calcined at 700° C. for a total of 3 hours in flowing air and then allowed to cool.

EXAMPLE 5

Thirteen thousand, five hundred and sixty five grams of $ZrO(NO_3)_2 \cdot xH_2O$ and 7,963 grams of $Ce(SO_4)_2$ were dissolved with stirring in 17,636 grams of distilled water. A second solution containing 4,055 grams of concentrated $NH_4OH$ and 30,096 grams of distilled water was prepared. These two solutions were combined at the rate of 500 ml/min using a nozzle mixing. The pH of the final composite was adjusted to approximately 8 by the addition of concentrated ammonium hydroxide. This slurry, having a solids content of about 7%, and was then aged in an autoclave at 100° C. for 72 hours. The product formed was recovered by filtration, washed with excess water, and stored as a filtercake. The filtercake was dried overnight at 120° C. Thereafter, the filtercake was calcined at 700° C. for a total of 3 hours in flowing air and then allowed to cool.

EXAMPLE 6

Comparative

Example 6 is a commercial ceria-zironia catalyst also containing sulfur, Product Code MI515 purchased from Grace Davison.

TABLE 1

| | Elemental Analyses of Calcined Materials | | | | | | | | |
|---|---|---|---|---|---|---|---|---|---|
| Example | Cerium % | Zirconium % | Sulfur % | Cerium moles | Zirconium moles | Sulfur moles | Ce n | Zr m | S p |
| 1 | 2.86 | 65.55 | 0.52 | 0.02 | 0.72 | 0.03 | 0.03 | 1.00 | 0.05 |
| 2 | 18.70 | 52.00 | 1.00 | 0.13 | 0.57 | 0.06 | 0.23 | 1.00 | 0.11 |
| 3 | 3.42 | 64.69 | 0.78 | 0.02 | 0.71 | 0.05 | 0.03 | 1.00 | 0.07 |
| 4 | 18.60 | 53.90 | 0.19 | 0.13 | 0.59 | 0.01 | 0.22 | 1.00 | 0.02 |
| 5 | 16.40 | 54.60 | 0.75 | 0.12 | 0.60 | 0.05 | 0.20 | 1.00 | 0.08 |
| 6 | 11.50 | 60.00 | 0.12 | 0.08 | 0.66 | 0.01 | 0.12 | 1.00 | 0.01 |

Elemental analysis of the samples were obtained using dispersive x-ray fluorescence (WDXRF) on a Siemens XRF, Model SRS 3000.

EXAMPLE 7–12

Performance Comparison.

The materials described in Examples 1–6 were tested for IPE conversion to IPA in Examples 7–12, respectively. The results are tabulated in Table 2 and are shown in FIG. 1.

The decomposition of IPE was investigated over each ctalyst of Examples 1–6 in a fixed-bed microreactor. 0.5 grams of each catalyst was loaded into a 3/8" O.D. stainless steel reactor and dried with $N_2$ at 210° C. A sample of isopropyl ether (IPE) from the Baton Rouge Chemical Plant (note: all IPE decomposition examples herein use the same grade of IPE, which comprises greater than 95 wt % IPE) was fed to the reactor at a WHSV of 5 h$^{-1}$. In addition, HPLC grade water was co-fed to the reactor at an IPE:$H_2O$ molar ratio of 1:1. Reactor temperature was about 210° C. and pressure was about 90 psig for each reaction. IPE conversion is defined as ($IPE_{product}$–$IPE_{feed}$)/$IPE_{feed}$, and IPA selectivity is defined as $IPA_{product}$/(Theoretical IPA produced from IPE decomposed). IPA Yield (Per Pass) is defined as the product of the IPE Conversion and the IPA Selectivity. Note: "Theoretical IPA produced" is the number of moles of IPA that are formed when a mole of IPE decomposes via reaction (1) above. Thus, if one mole of IPE decomposes to form 1 mole of IPA and 1 mole of propylene, then the IPA selectivity would be equal to 100%. If less than one mole of IPA is produced, e.g., due to subsequent dehydration of the IPA to propylene, then IPA selectivity would be less than 100%. If additional IPA is formed, e.g, by hydration of the propylene formed back to IPA, then IPA selectivity could be greater than 100%.

The reactor was run for a length of time sufficient to determine the maximum IPA yield. The maximum yields are tabulated in Table 2, below, and also shown graphically in FIG. 1.

These experiments show the unique character of the composition with regard to the amount of sulfur present, especially in and around the level of about 0.50 to about 1.25 wt %, more preferably in the amount of from about 0.65 to less than 1.00 wt %, still more preferably in the amount of from about 0.65 wt % to about 0.85 wt %, and yet still more preferably about 0.75 wt % sulfur.

TABLE 2 wt % sulfur and IPA yield

| Example | Catalyst of Example | S, wt % | Max IPA Yield |
|---|---|---|---|
| 7 | 1 | 0.52 | 27 |
| 8 | 2 | 1.00 | 44 |
| 9 | 3 | 0.78 | 51 |
| 10 | 4 | 0.19 | 9 |
| 11 | 5 | 0.75 | 59 |
| 12 | 6 | 0.12 | 0 |

The "Max IPA Yield" is determined by plotting IPA yield versus IPE converison. Such a plot goes through a maximum, which is the number reported.

Note that the commercially available catalyst was inactive for IPA production.

EXAMPLE 13

Diffuse Reflectance Infrared Spectroscopy (DRIFTS) Characterizations

The type of sulfur species and acid sites present in ceria-sulfur-zirconia samples described in Examples 1 through 6 were studied by DRIFTS. DRIFTS spectra were recorded on a Nicolet Magna-IR 560 spectrometer equipped with an in situ DRIFTS cell. Samples were prepared in the conventional manner. The spectral resolution was 4 cm$^{-1}$.

Figure 2:
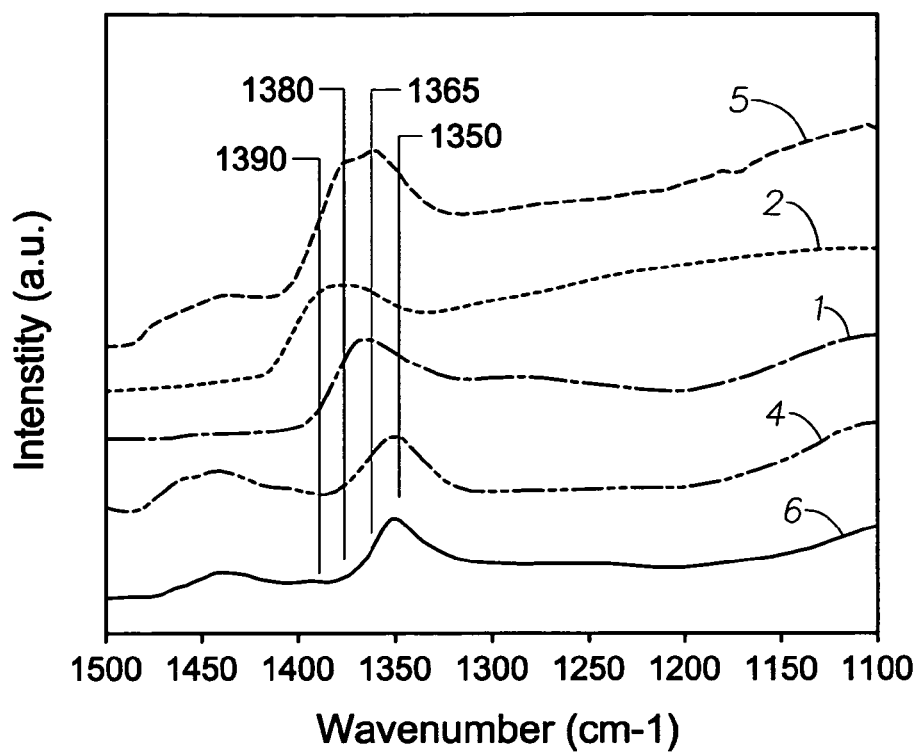
FIGS. 2 shows DRIFTS spectra for cerium zirconium mixed oxides in the region of 1500–1100 cm$^{-1}$.
Figure 3:
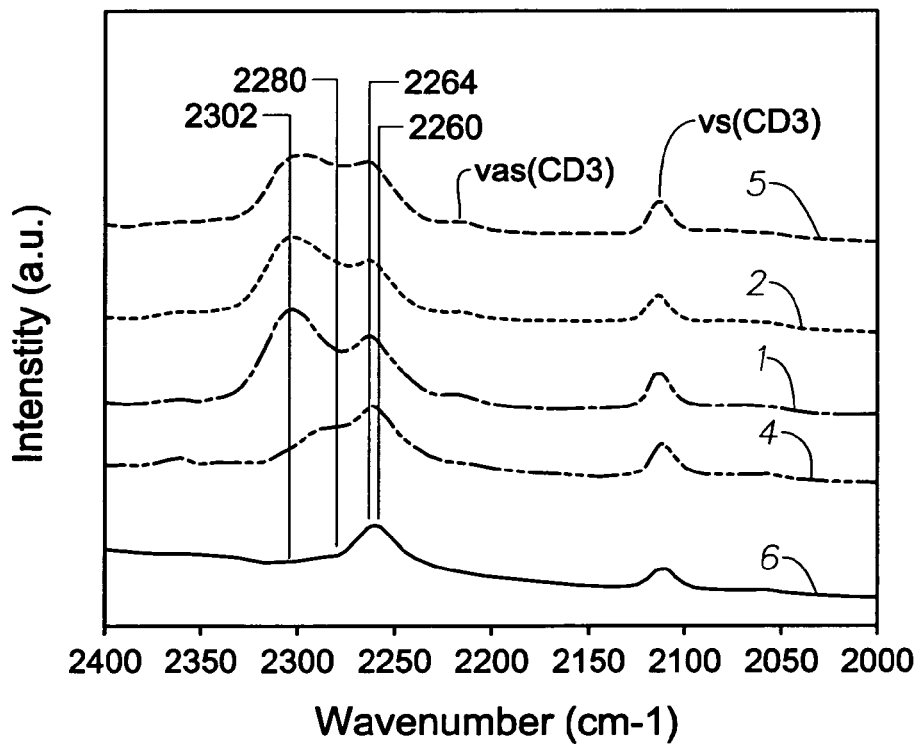
FIG. 3 shows DRIFTS spectra for cerium zirconium oxides after adsorption of CD$_3$CN in the region of 2400–2000 cm$^{-1}$.

The results are shown in FIG. 2 and FIG. 3.

FIG. 2 shows DRIFTS spectra in the region of 1500–1100 cm$^{-1}$ of the sulfur species in the ceria-sulfur-zirconia samples. The samples were first calcined in 9 vol % $O_2$ in He at 250° C. for 1 h, then cooled down in He to 50° C. As can be seen, the DRIFTS spectra show strong bands in the range of 1400–1300 cm$^{-1}$. These bands are correlated with S=O stretching vibrations (C. Morterra, G. Cerrato, V. Bolis, Catal. Today 17 (1993) 505). With a low sulfur loading, the S=O band is observed at 1350 cm$^{-1}$ but shift to higher wavenumber (e.g. 1365–1390 cm$^{-1}$) with a high sulfur loading. This DRIFTS spectra suggest the formation different oxy-sulfur species on the samples. From a catalytic point of view, catalysts producing the best IPA yields have surface sulfur species with S=O stretching vibrations in the range of 1420–1300 cm$^{-1}$, preferably 1365–1390 cm$^{-1}$.

FIG. 3 shows DRIFTS spectra in the region of 2400–2000 cm$^{-1}$ after adsorption of deuterated acetonitrile ($CD_3CN$) on the ceria-sulfur-zirconia samples. This technique is known in the literature and has been used as a spectroscopic probe to characterize the acidity of metal oxides. When the molecule is free, the ν(CN) vibration of the CD3CN is observed at around 2260cm$^{-1}$. However, the ν(CN) wavenumber increases when electron donor-acceptor complexes [CD3CN . . . A] are formed (A representing an acid site; Bronsted or Lewis). Detailed information about the use of this technique can be found in C. Morterra, M. Penarroya Mentruit and G. Cerrato, Phys. Chem. Chem. Phys., 2002, 4, 676; Escalona Platero, M. Pearroya Mentruit and C. Morterra, Langmuir, 1999, 15, 5079; P. Scokart, F. Declerck, R. Semples and P. Rouxhet, J. Chem. Soc. Faraday Trans. 1, 1977, 73, 359; Z. Tvaruzkova, K. Habersberger and p. Jiru, React. Kinet. Catal. Lett., 1991, 44, 361; H. Knoezinger and H. Krietenbrink, J. Chem. Soc. Faraday Trans. 1, 1975, 71, 2421.

Before adsorption of $CD_3CN$, the samples were first calcined in 9 vol % $O_2$ in He at 250° C. for 1 h, then cooled down in He to 50° C. $CD_3CN$ adsorption was carried out at 50° C. in He flow for 15 min. DRIFTS spectra were taken after purging the samples with pure He at 50° C. for 15 min in order to remove physisorbed $CD_3CN$.

When the $CD_3CN$ is adsorbed on ceria-zirconia the ν(CN) vibration is observed in the range of 2260–2302 cm$^{-1}$. The shift of the ν(CN) vibration to higher wavenumbers (e.g. >2260 cm$^{-1}$) is attributed to the coordination of $CD_3CN$ with acid sites. These shifts of the ν(CN) to higher wavenumbers are correlated with an increase in the acid sites strength and sulfur content. A high IPA yield corresponds with samples having a ν(CN) IR vibrations in the range of 2340–2280 cm$^{-1}$ and more preferably having two peaks, one at about 2302 cm$^{-1}$ and one at about 2264 cm$^{-1}$.

The results of the DRIFTS experiments shows a multiplicity of acid sites, with one peak in the vicinity of 2300 cm$^{-1}$ indicating one type of acidity and another peak at 2260 cm$^{-1}$ indicating another type of acidity. The intensity of these peaks are roughly in balance for the optimal catalyst.

According to the literature, cited elsewhere herein, these peaks are ascribed to different acidity types, i.e., Bronsted and Lewis sites, although the inventors do not wish to speculate as to which peak indicates which type of acidity. Nevertheless, while not wishing to be bound by theory, these findings appear to indicate that a optimum concentration of surface oxy-sulfur species and a balance of acid sites are necessary for high selectivity towards alcohols when converting ethers back to their corresponding alcohols in the presence of water.

EXAMPLE 14

Acidity Characterizations Using 1-aminopropane (n-propylamine) Decomposition

Some of the samples described in Examples 1–5 above were also characterized for acid site distribution and strength based on the temperature(s) at which decomposition of n-propylamine (to propene, ammonia and water) occurs. This technique is known in the literature and has been used to elucidate acidity in work conducted by R. J. Gorte and G. L. Price. See, for instance, Grady, M. C. and Gorte, R. J., *J. Phys. Chem.* 89, 1305 (1985); Aronsom, M. T., Gorte, R. J., and Farneth, W. E., *J. Catal.* 98, 434 (1986); Gricus Kofke, T. J., Gorte, R. J., and Farneth, W. E., *J. Catal* 114, 34 (1988); Gricus Kofke, T. J., and Gorte, R. J., *J. Catal* 115, 233 (1989); Gricus Kofke, T. J., Gorte, R. J., and Kokotailo, G. T., *Appl. Catal.* 54, 177 (1989); Gricus Kofke, T. J., Gorte, R. J., and Kokotailo, G. T., *J. Catal.* 116, 252 (1989); Parrillo, D. J., Adamo, A. T., Kokotailo, G. T., and Gorte, R. J., *Appl. Catal.* 67, 107 (1990); Biaglow, A. I., Adamo, A. T., Kokotailo, G. T. and Gorte, R. J., *J. Catal.* 131, 252 (1991); Parillo, D. J., Pereira, C., Kokotailo, G. T., and Gorte, R. J., *J. Catal.* 138, 377 (1992); Kanazirev, V., Dooley, K. M. and Price, G. L., *J. Catal.* 146, 228 (1994); and Kanazirev, V., Dooley, K. M. and Price, G. L., *Catalysis Letters* 24, 227 (1994).

Details of the characterization method used are as follows. The evaluation sample is placed into a sample cell and heated to 200° C. at a rate of 3–5 cc/min in flowing helium (typical flow of 25–30 cc/min). The temperature is maintained for 1-hour to remove physisorbed water. The sample is cooled under flowing helium to 50° C. and held at this temperature for a minimum of 5 minutes. A stream of 1-aminopropane saturated helium (obtained by directing the helium stream through a saturator vessel containing 1-aminoproane liquid with sparger tube in series before the sample cell) is sent through the sample cell. After 5 minutes, the saturator is removed from the gas stream. The sample, maintained at 50° C., is purged with helium for 30 minutes after exposure to the saturator. The temperature is ramped at a rate of 3–4 cc/min from 50° C. to 750° C. and held at this maximum temperature for 30 minutes. Thermal Conductivity Response (TCD) of the effluent stream from the sample cell is monitored during the 50–750° C. heating step to measure ammonia as the decomposition product from the 1-aminopropane sorbed on the sample and determine acidity of the sample.

As used herein, the phrase "Acidity Characterization using 1-Aminopropane Decomposition" means the acidity characterization using the aforementioned procedure.

Figure 4:
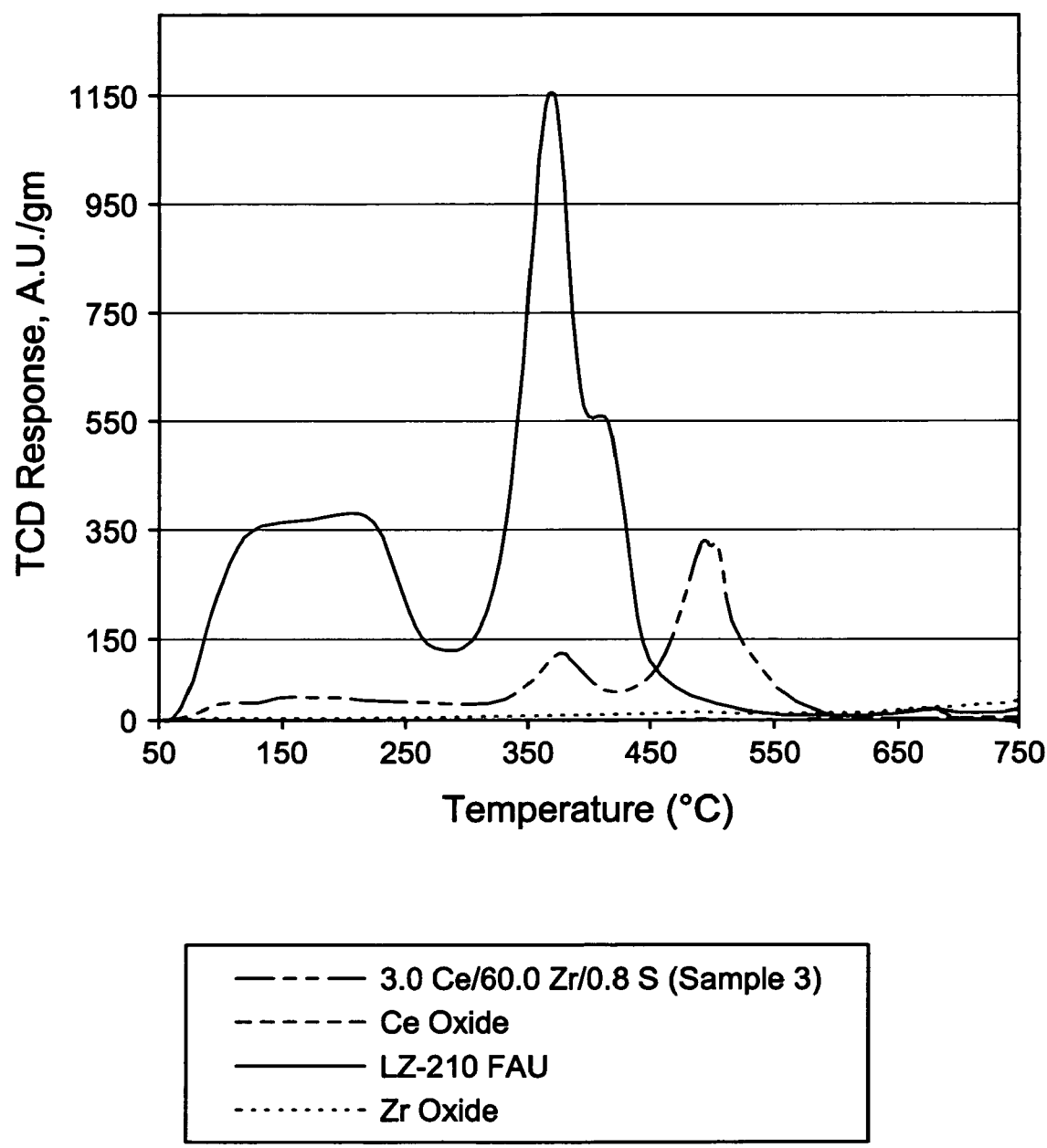
FIGS. 4 and 5 show the Acidity Characterization using 1-Aminopropane Decomposition of catalysts according to the present invention and other catalysts.

FIG. 4 compares the acidity of a composition according to the present invention (sample #3 in the tables above), with that of a Faujasite type zeolite, LZ-210 FAU, purchased from Katalistiks but readily available as a standard for this type of measurement from numerous commercial sources. The acidity measured for the composition according to the present invention is markedly different and exhibits a higher temperature component (>450° C.) than the zeolite. Cerium and zirconium oxides alone are shown to have no acidity (their response lines are barely visible in FIG. 4), demonstrating the importance of the addition of sulfur to produce a material active toward IPE conversion to IPA.

Figure 5:
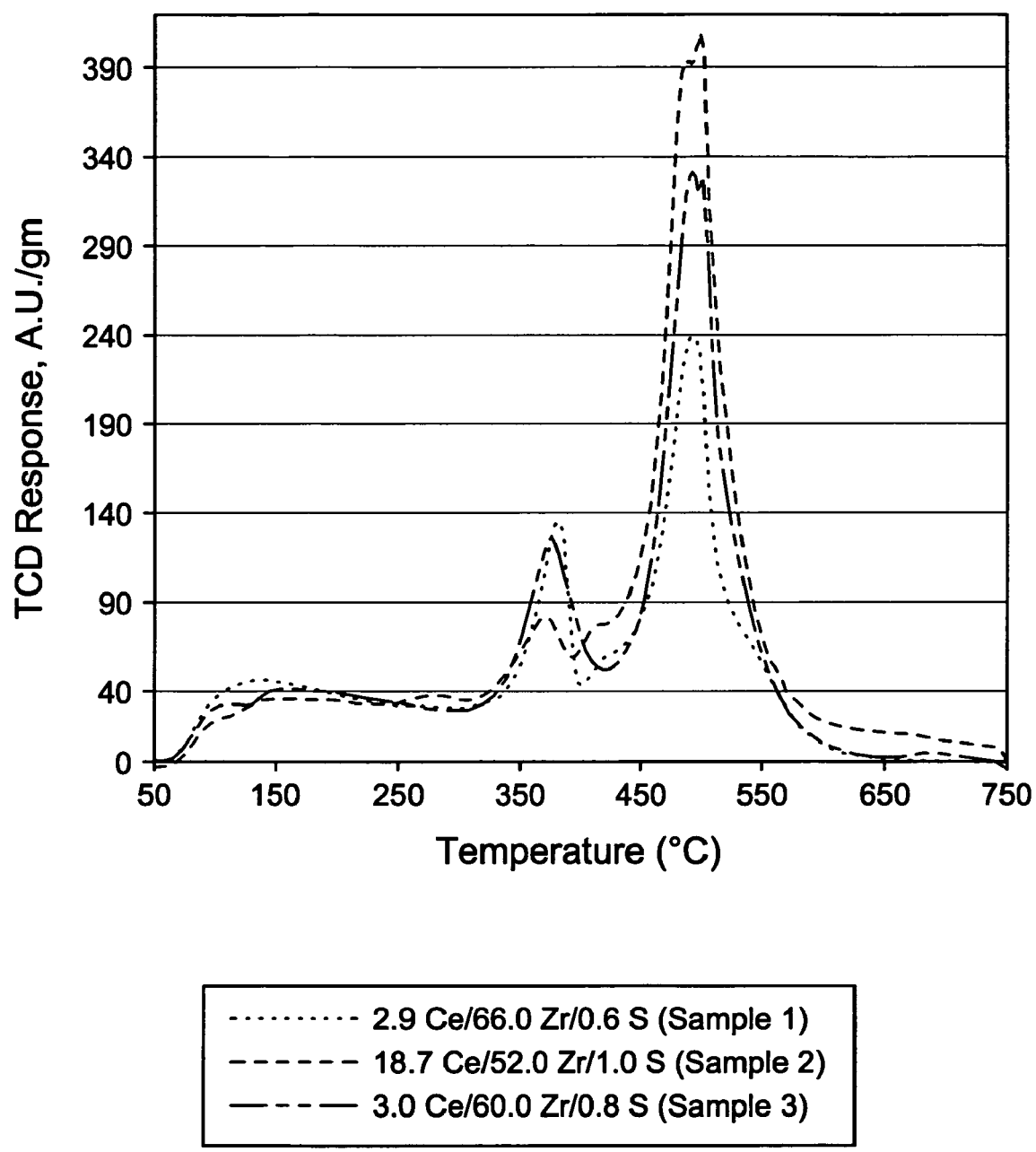

FIG. 5 compares the acidities of several different compositions according to the present invention for IPE conversion to IPA. Based on these acidities, it is suggested that there must be a proper balance between acidity in the temperature range of about 300 to about 450° C. and for activity at temperatures greater than about 450° C. to optimize conversion. For the samples evaluated, the preferred ratio of 300–450° C. to >450° C. acidity is less than about 0.5 based on approximate peak height of the largest peaks in that temperature range (as can simply be measured from the graph). Acidity measured <~250–300° C. is residual 1-aminopropane and is not considered to be important for CeZrSO materials.

Trade names used herein are indicated by a ™ symbol or ® symbol, indicating that the names may be protected by certain trademark rights, e.g., they may be registered trademarks in various jurisdictions.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

While the illustrative embodiments of the invention have been described with particularity, it will be understood that many variations will suggest themselves to those skilled in this art in light of the above detailed description. All such obvious variations are within the full intended scope of the appended claims. Preferred embodiments include: A composition comprising a compound having the following empirical formula (1):

$$X_m Y_n S_p O_q \tag{1}$$

where X is at least one metal selected from Group 4 of the Periodic Table of Elements, Y is at least one metal selected from Group 3 (including the Lanthanides and Actinides) of the Periodic Table of Elements, and S is sulfur; m, n, p and q are the atomic ratios of their respective components and, when m is 1, n is from about 0.01 to about 0.75, p is from about 0.01 to about 0.50, q is the number of oxygen atoms necessary to satisfy the valence of the other components, further characterized as containing a sulfur species with DRIFTS S=O stretching vibrations in the range of 1365–1390 cm$^{-1}$, and which may be further characterized by one or more of the following: wherein n is from 0.01 to about 0.35; p is from about 0.05 to about 0.35; wherein p is from about 0.10 to about 0.30; wherein p is from about 0.10 to about 0.20; wherein sulfur is present in the amount of about 0.50 to 1.25 wt %, based on the total weight of the compound according to formula (1); wherein sulfur is present in the amount of about 0.55 to less than 1.00 wt %, based on the total weight of the compound according to formula (1); wherein sulfur is present in the amount of about 0.65 to 0.85 wt % based on the total weight of the compound according to formula (1); wherein, after CD$_3$CN adsorption, the compound of formula (1) has at least one DRIFTS ν(CN) IR vibration after in the range 2280–2330 cm$^{-1}$, more particularly having at least two IR absorption peaks for ν(CN), one at one at about 2302 cm$^{-1}$ and one at about 2264 cm$^{-1}$; further characterized by an Acidity Characterization using 1-Aminopropane Decomposition having at least two Thermal Conductivity Response components, at least one component being between about 300° C. and 450° C. and at least one component at greater than 450° C.; and also the preferred embodiment of a method of making IPA comprising contacting IPE with a composition comprising a compound having the following empirical formula (1):

$$X_m Y_n S_p O_q \quad (1)$$

where X is at least one metal selected from Group 4 of the Periodic Table of Elements, Y is at least one metal selected from Group 3 (including the Lanthanides and Actinides) of the Periodic Table of Elements, and S is sulfur; m, n, p and q are the atomic ratios of their respective components and, when m is 1, n is from about 0.01 to about 0.75, p is from about 0.01 to about 0.50, q is the number of oxygen atoms necessary to satisfy the valence of the other components, further characterized as containing a sulfur species with DRIFTS S=O stretching vibrations in the range of 1365–1390 cm$^{-1}$; which may also be modified in the same manner as for the composition embodiments set forth herein, for example wherein n is from 0.01 to about 0.35; p is from about 0.05 to about 0.35; wherein p is from about 0.10 to about 0.30; wherein p is from about 0.10 to about 0.20; wherein sulfur is present in the amount of about 0.50 to 1.25 wt %, based on the total weight of the compound according to formula (1); wherein sulfur is present in the amount of about 0.55 to less than 1.00 wt %, based on the total weight of the compound according to formula (1); wherein sulfur is present in the amount of about 0.65 to 0.85 wt % based on the total weight of the compound according to formula (1); wherein, after CD$_3$CN adsorption, the compound of formula (1) has at least one DRIFTS ν(CN) IR vibration after in the range 2280–2330 cm$^{-1}$, more particularly having at least two IR absorption peaks for ν(CN), one at one at about 2302 cm$^{-1}$ and one at about 2264 cm$^{-1}$; further characterized by an Acidity Characterization using 1-Aminopropane Decomposition having at least two Thermal Conductivity Response components, at least one component being between about 300° C. and 450° C. and at least one component at greater than 450° C.; and also a preferred embodiment of a method of decomposing an ether to the corresponding alkanol and alkene comprising contacting said ether with the composition according to any of the aforementioned composition embodiments, or the following composition embodiments, which also represent yet another preferred embodiment: a composition comprising a compound having the following empirical formula (1):

$$X_m Y_n S_p O_q \quad (1)$$

where X is at least one metal selected from Group 4 of the Periodic Table of Elements, Y is at least one metal selected from Group 3 (including the Lanthanides and Actinides) of the Periodic Table of Elements, and S is sulfur; m, n, p and q are the atomic ratios of their respective components and, when m is 1, n is from about 0.01 to about 0.75, p is from about 0.01 to about 0.50, q is the number of oxygen atoms necessary to satisfy the valence of the other components, further characterized as containing a multiplicity of acid sites; especially such a composition wherein said compound is further characterized by at least one of the following:

(a) plural S=O stretching vibrations in the spectral region of 2260 to 2350 cm$^{-1}$ as obtained by DRIFTS;

(b) wherein, after CD$_3$CN adsorption, the compound of formula (1) has at least one DRIFTS ν(CN) IR vibration after in the range 2280–2330 cm$^{-1}$;

(c) having at least two IR absorption peaks for ν(CN), one at one at about 2302 cm$^{-1}$ and one at about 2264 cm$^{-1}$;

(d) an Acidity Characterization using 1-Aminopropane Decomposition having at least two Thermal Conductivity Response components, at least one component being between about 300° C. and 450° C. and at least one component at greater than 450° C.

We claim:

1. A method of making IPA comprising contacting IPE with a composition comprising a compound having the following empirical formula (1):

$$X_m Y_n S_p O_q \quad (1)$$

where X is at least one metal selected from Group 4 of the Periodic Table of Elements, Y is at least one metal selected from Group 3 (including the Lanthanides and Actinides) of the Periodic Table of Elements, and S is sulfur; m, n, p and q are the atomic ratios of their respective components and, when m is 1, n is from about 0.01 to about 0.75, p is from about 0.01 to about 0.50, q is the number of oxygen atoms necessary to satisfy the valence of the other components, further characterized as containing a sulfur species with DRIFTS S=O stretching vibrations in the range of 1365–1390 cm$^{-1}$.

2. The method of claim 1, wherein n is from 0.01 to about 0.35; and p is from about 0.05 to about 0.35.

3. The method of claim 2, wherein p is from about 0.10 to about 0.30.

4. The method of claim 2, wherein p is from about 0.10 to about 0.20.

5. The method of claim 1, wherein sulfur is present in the amount of about 0.50 to 1.25 wt %, based on the total weight of the compound according to formula (1).

6. The method of claim 1, wherein sulfur is present in the amount of about 0.55 to less than 1.00 wt %, based on the total weight of the compound according to formula (1).

7. The method of claim 1, wherein sulfur is present in the amount of about 0.65 to 0.85 wt % based on the total weight of the compound according to formula (1).

8. The method of claim 1, wherein, after CD$_3$CN adsorption, the compound of formula (1) has at least one DRIFTS ν(CN) IR vibration in the range 2280–2330 cm$^{-1}$.

9. The method of claim 8, having at least two IR absorption peaks for ν(CN), one at one at about 2302 cm$^{-1}$ and one at about 2264 cm$^{-1}$.

10. The method of claim 1, further characterized by an Acidity Characterization using 1-Aminopropane Decomposition having at least two Thermal Conductivity Response components, at least one component being between about 300° C. and 450° C. and at least one component at greater than 450° C.

11. A method of decomposing an ether to the corresponding alkanol and alkene comprising contacting said ether with a composition comprising a compound according to the following empirical formula (1):

$$X_m Y_n S_p O_q \quad (1)$$

where X is at least one metal selected from Group 4 of the Periodic Table of Elements, Y is at least one metal selected from Group 3 (including the Lanthanides and Actinides) of the Periodic Table of Elements, and S is sulfur; m, n, p and q are the atomic ratios of their respective components and, when m is 1, n is from about 0.01 to about 0.75, p is from about 0.01 to about 0.50, q is the number of oxygen atoms necessary to satisfy the valence of the other components, further characterized as containing a sulfur species with DRIFTS S=O stretching vibrations in the range of 1365–1390 cm$^{-1}$.

* * * * *